(12) United States Patent
Morris et al.

(10) Patent No.: US 9,700,475 B2
(45) Date of Patent: Jul. 11, 2017

(54) CONTROLLING ACCESS TO RADIOTHERAPY SYSTEMS

(71) Applicant: Elekta AB (publ), Stockholm (SE)

(72) Inventors: Anthony Paul Morris, Warwick (GB); Alexander John Baker, Warwick (GB); Alexander James Woolley, Warwick (GB); Daniel Paul Jenkins, Warwick (GB); Sarah Witheford, Warwick (GB); Timothy Lewis Sharpe, Warwick (GB); John David Cross, Warwick (GB); Malcolm Stanley Boyd, Warwick (GB)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 15/147,011

(22) Filed: May 5, 2016

(65) Prior Publication Data
US 2016/0242980 A1    Aug. 25, 2016

Related U.S. Application Data

(63) Continuation of application No. 14/094,034, filed on Dec. 2, 2013, now Pat. No. 9,358,405.

(51) Int. Cl.
| | | |
|---|---|---|
| *G06F 17/00* | (2006.01) | |
| *A61G 13/02* | (2006.01) | |
| *A61N 5/10* | (2006.01) | |
| *G06Q 50/24* | (2012.01) | |
| *A61B 90/98* | (2016.01) | |
| *A61B 6/04* | (2006.01) | |
| *G06K 17/00* | (2006.01) | |
| *A61B 90/90* | (2016.01) | |

(52) U.S. Cl.
CPC .......... *A61G 13/02* (2013.01); *A61B 90/98* (2016.02); *A61N 5/1045* (2013.01); *A61N 5/1048* (2013.01); *A61N 5/1081* (2013.01); *G06Q 50/24* (2013.01); *A61B 6/0407* (2013.01); *A61B 90/90* (2016.02); *A61G 2210/50* (2013.01); *A61N 2005/1074* (2013.01); *A61N 2005/1087* (2013.01); *A61N 2005/1089* (2013.01); *G06K 2017/009* (2013.01)

(58) Field of Classification Search
USPC ................... 235/382; 5/600, 616; 600/439
See application file for complete search history.

(56) References Cited

U.S. PATENT DOCUMENTS

| | | | |
|---|---|---|---|
| 7,962,981 B2* | 6/2011 | Lemire | A61G 7/005 5/600 |
| 9,041,531 B1 | 5/2015 | DeLand | |
| 2005/0185766 A1* | 8/2005 | Tsujita | A61N 5/1042 378/150 |

(Continued)

FOREIGN PATENT DOCUMENTS

| | | |
|---|---|---|
| WO | WO 2005/106813 | 11/2005 |
| WO | WO 2012/045643 | 4/2012 |

*Primary Examiner* — Daniel Hess
(74) *Attorney, Agent, or Firm* — Sunstein Kann Murphy & Timbers LLP

(57) ABSTRACT

A patient support includes a bed, one or more mechanisms configured for manipulating at least one of position and orientation of the bed, and a display configured for displaying a user interface and receiving inputs to control at least the one or more mechanisms.

12 Claims, 5 Drawing Sheets

(56) References Cited

U.S. PATENT DOCUMENTS

| | | | |
|---|---|---|---|
| 2008/0009731 A1* | 1/2008 | Maschke | A61B 5/6833 600/439 |
| 2008/0029369 A1 | 2/2008 | Weigold | |
| 2008/0172789 A1* | 7/2008 | Elliot | A61G 7/0528 5/616 |
| 2009/0079576 A1 | 3/2009 | Yankelevitz | |
| 2010/0067660 A1 | 3/2010 | Maurer, Jr. et al. | |
| 2011/0133903 A1 | 6/2011 | Alsafadi | |
| 2013/0188629 A1 | 7/2013 | Lemaire | |
| 2014/0084058 A1 | 3/2014 | Barry | |

\* cited by examiner

CONTROLLING ACCESS TO RADIOTHERAPY SYSTEMS

This application is a continuation of U.S. patent application Ser. No. 14/094,034, filed Dec. 2, 2013, which is incorporated herein by reference in its entirety.

TECHNICAL FIELD

The present invention relates to radiotherapy, and particularly to methods, apparatus and systems for controlling access to a radiotherapy system.

BACKGROUND

Radiotherapy involves the production of a beam of high-energy ionising radiation, usually x-rays or a beam of electrons or other sub-atomic particles. This is directed towards a target region of the patient, and adversely affects the target cells (typically tumour cells) causing an alleviation of the patient's symptoms.

In order to ensure that the radiation is delivered to the patient safely, radiotherapy treatment is necessarily a complex process involving many steps. As part of that process, a number of different personnel may have cause to use the machine for different reasons, but not all will generally need access to the same machine parameters. For example, a radiotherapy technician may need to control the system directly to deliver a particular plan of treatment, whereas a nurse may need only to access the system to position a patient on the patient support. Similarly, a repair and maintenance technician may need to access parameters which are generally not available to others. It would therefore be useful to gain a measure of control over who can issue commands to the radiotherapy system, and ensure that each command has been issued by a person of appropriate qualifications.

It would also be advantageous to design a medical environment with minimal exposed keys and protruding surfaces. Various fluids may be involved in the treatment process, which could get caught on levers and pulleys, or may be spilt accidentally. A system which can withstand such accidents will in general be able to maintain an operative state for a longer period of time.

SUMMARY OF INVENTION

According to a first aspect of the present invention, there is provided a patient support that includes a bed, one or more mechanisms configured for manipulating at least one of position and orientation of the bed, and a display configured for displaying a user interface and receiving inputs to control at least the one or more mechanisms.

In further specific embodiments, the display may be provided on an edge of the bed, which may be located at the head of the bed or the foot of the bed. The edge of the bed may be sloped with respect to a plane of the bed. There may be a mechanism configured for detecting the presence of a control device on the display and/or a mechanism configured for detecting an orientation of a control device on the display. There may be a detection system configured for determining an identity of a user of a control device on the display, and the display may be configured to display input controls that are specific to the identity of the user determined by the detection system.

According to a second aspect of the invention, there is provided a radiotherapy system with a source of radiation configured to generate a beam of radiation, one or more collimating mechanisms configured to selectively delimit an extent of the beam of radiation, and a patient support. The patient support is configured for supporting a patient undergoing radiotherapy, and includes a bed and a display configured for displaying a user interface and receiving inputs to control at least one of the source of radiation, the one or more collimating mechanisms, and the patient support.

In further specific embodiments, the display may be located on a console that is separate from the patient support. The patient support may include the display. There may be a mechanism for detecting the presence of a control device on the display and/or a mechanism configured for detecting an orientation of a control device on the display. There may be a detection system configured for determining an identity of a user of a control device on the display. And the display may be configured to display input controls that are specific to the identity of the user determined by the detection system. The one or more collimating mechanisms may be a multi-leaf collimator.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

To address the concerns noted above, a new device or "key" is provided to each radiotherapy professional. In some embodiments, the device may be used as a control device, to input commands to various devices and equipment in the therapy suite, for example by cooperating with one or more control screens. The device may contain a wireless beacon so that it can be located precisely within the suite, and contain identity data corresponding to the user of the device, so that only those controls suitable for the professional concerned are available.

Figure 1:
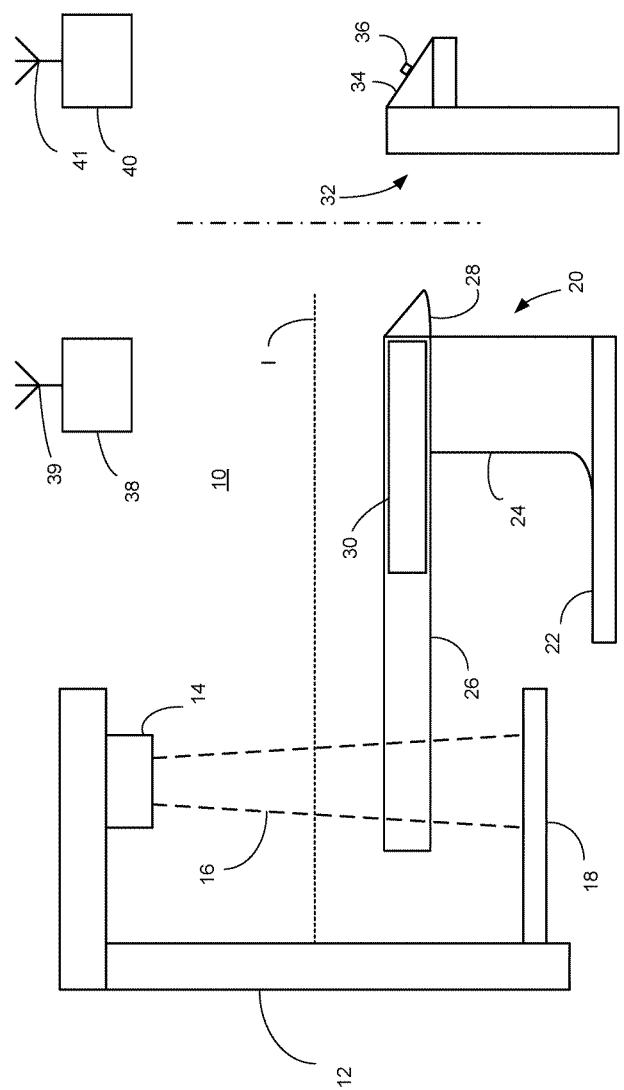
FIG. 1 shows a radiotherapy system comprising a control mechanism according to embodiments of the present invention.

FIG. 1 is a schematic drawing showing a side view of a radiotherapy system 10 according to embodiments of the present invention. Treatment components of the system 10 (i.e. those which deliver the therapeutic radiation) are shown on the left-hand side of the drawing, while control components of the system 10 (i.e. those which control the treatment components) are shown on the right-hand side. This arrangement reflects the provision of a therapy machine in one room and a control mechanism for the machine in another, adjacent room. The two rooms may be linked by a window allowing a technician to view the treatment as it is carried out. In some embodiments, however, some or all of the controls may be provided in the treatment room, i.e., the controls could be split between treatment and control rooms, or there may be no separate control room.

The system 10 comprises a rotatable gantry 12 which is able to rotate about an axis I. Mounted on the gantry 12 is a radiation head 14, which provides a beam of radiation 16 directed generally towards and intersecting the axis I. In this way, a target placed at the point of intersection between the axis I and the beam 16 (commonly referred to as the isocenter) can be made to lie within the beam's extent at all angles of rotation of the gantry 12. Radiation dose therefore builds to a relatively high level there while remaining relatively low in the surrounding volume, which lies within the beam's extent only at certain angles of rotation.

The radiation head 14 may comprise, or be connected to one or more sources of therapeutic radiation (not illustrated), such as a linear accelerator or a radioactive isotope (e.g. cobalt 60). The beam 16 can be formed from any suitable ionizing radiation, such as protons, electrons or x-rays.

The radiation head 14 may comprise one or more collimators (not illustrated) for collimating and shaping the beam 16. The radiation head 14 may comprise one or more primary collimators which collimate the beam to take a regular geometric shape (e.g. cone beams, fan beams etc), and one or more secondary collimators to act dynamically on the regular-shaped beam so that it can have different cross-sections at different angles of rotation. That is, in general the target will not have the same profile at all angles of rotation, and the beam can be adapted to conform to that profile or take some other desirable shape as required. Multi-leaf collimators are well known secondary collimators for performing this task.

An imaging panel 18 is also mounted to the gantry 12, in a position generally opposite to that of the radiation head 14. The panel 18 is positioned so as to intersect the radiation beam 16 after it has passed through the target, and can therefore provide information on the treatment as it is progressing. For example, the panel 18 can provide images of the radiation beam 16 (so-called "portal images") which can be used to check the shape of the beam 16 and its position relative to anatomical structures within the patient (i.e. ensuring that the beam has an expected shape and is correctly positioned with respect to the target). The imaging data acquired by the panel 18 can also be used to build three-dimensional images of the target using CT techniques.

Figure 2:
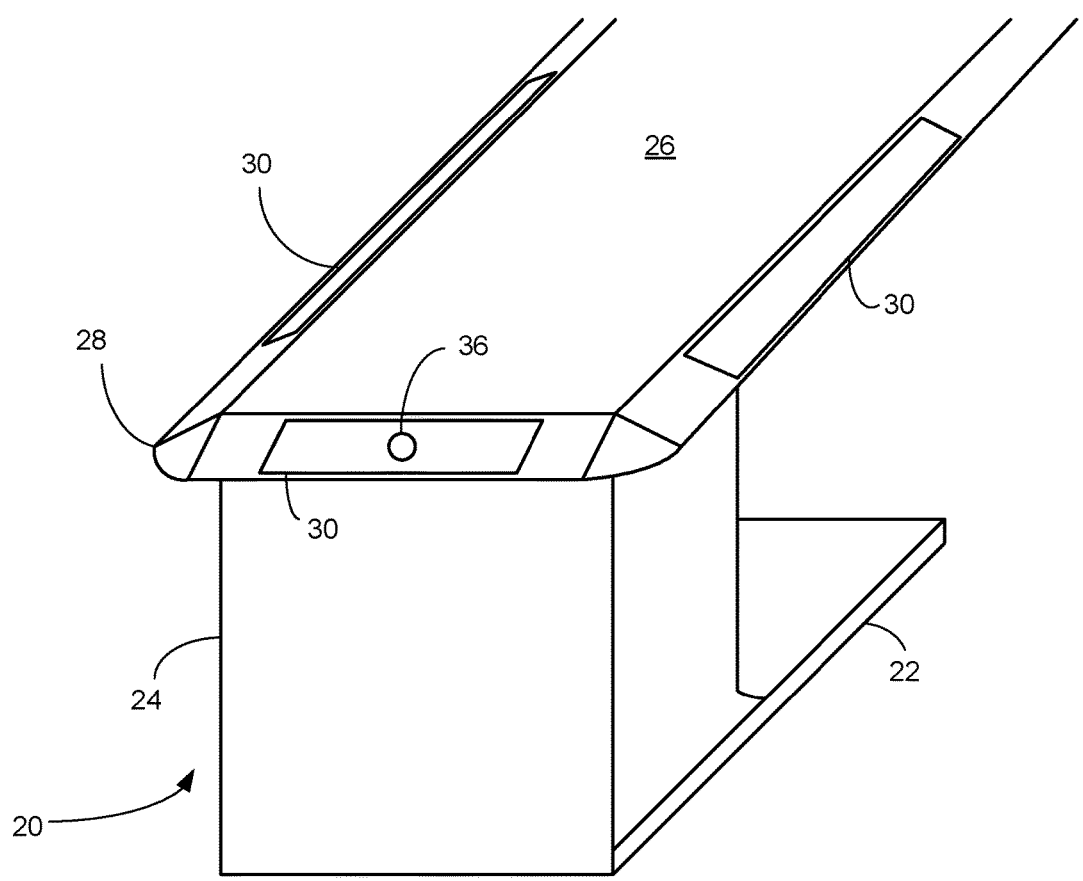
FIG. 2 shows a partial view of a patient support according to embodiments of the present invention.

Referring now to FIG. 2 as well as FIG. 1, a patient support 20 is provided to ensure the patient is supported and comfortable throughout treatment, but also to ensure the patient is positioned correctly so that the radiation beam 16 is accurately directed towards the target. For example, the support 20 may be able to position the patient in up to six degrees of freedom: x, y, z, pitch, yaw and roll. In the illustrated embodiment, the support 20 comprises a base 22, a support mechanism 24 and a bed 26. The base 22 is in connection with the ground, and may be able to move in one or two dimensions so as to vary the position of the support 20 relative to the gantry 12. The support mechanism 24 connects the bed 26 to the base 22, and may be able to vary one or more of the height, pitch, yaw and roll of the bed 26 with respect to the base 22.

The bed 26 is primarily for supporting the patient and comprises a substantially flat rectangular surface for that purpose. One or more cushions may also be provided for comfort. In the illustrated embodiment, the bed further comprises a sloping edge 28 extending from one or more edges of the bed 26. In some embodiments the sloping edge 28 extends from more than one edge of bed, and in other embodiments still the sloping edge 28 extends from three edges of the bed: the two long edges of the bed 26 and the shorter edge furthest from the radiation beam 16 (see FIG. 2). According to some embodiments of the invention, one or more control screens 30 are arranged on the sloping edge 28. The system 10 may comprise a single control screen 30, or multiple control screens arranged around multiple edges of the bed 26. In one embodiment (see FIG. 2), a control screen 30 is arranged on the sloping edge 28 on each of three edges of the bed: the two long edges of the bed 26 and the shorter edge furthest from the radiation beam 16. The control screens 30 may be used to control the system 10 in a manner to be described in greater detail below. The screen 30 comprises a display and one or more mechanisms for detecting the presence and orientation of a control device, as will be described below. In other embodiments, the control screens may be arranged on a console adjacent to and separate from the patient support 20 rather than on one or more edges of the bed 26. The height of the console and the patient support may be adjusted separately as required by the user.

In the control room, a control console 32 allows a technician to control the system 10. The console 32 comprises a control screen 34, and this is similar in construction and operation to the control screens 30 positioned around the patient bed 26. A control device 36 is placed on the control screen 34, and cooperates with it to input signals from a technician to control the system 10. The control device 36 can also be placed on the control screens 30, next to the patient bed, in order to control the system in a similar manner. Again, this aspect will be described in greater detail below.

The control device 36 comprises a wireless beacon (not illustrated in FIGS. 1 and 2), which can be detected in order to localize the device's position in the treatment and/or control rooms. In the treatment room, therefore, a detection system 38 is provided having one or more antennas 39, in order to detect the presence and location of the control device 36. In the control room, a similar detection system 40 is provided, also having one or more antennas 41.

Figure 3A:
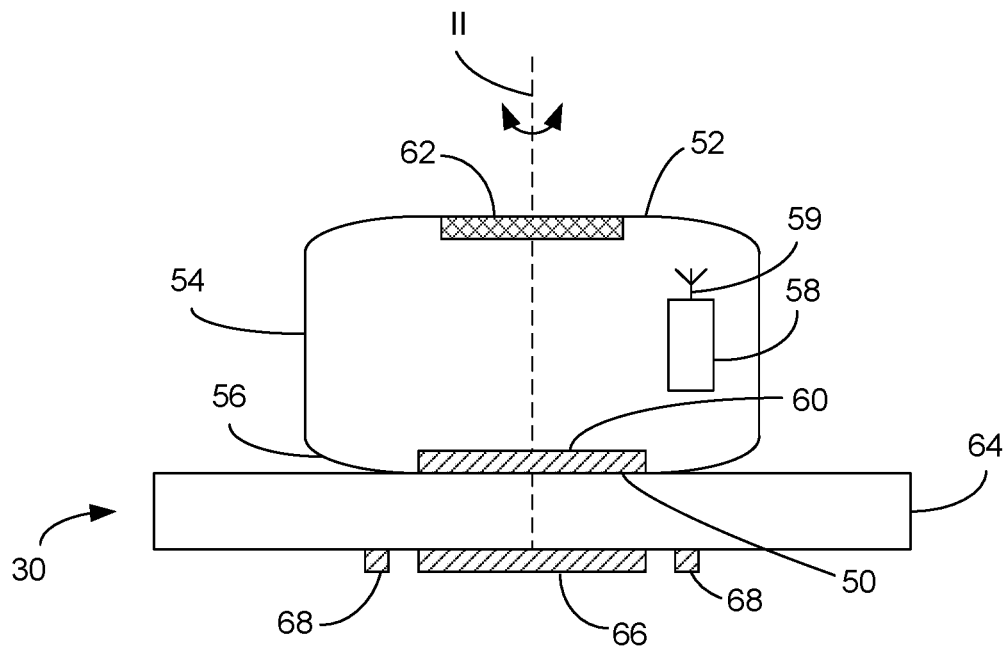
FIGS. 3a and 3b are cross-section views showing operation of the control mechanism according to embodiments of the present invention.
Figure 3B:
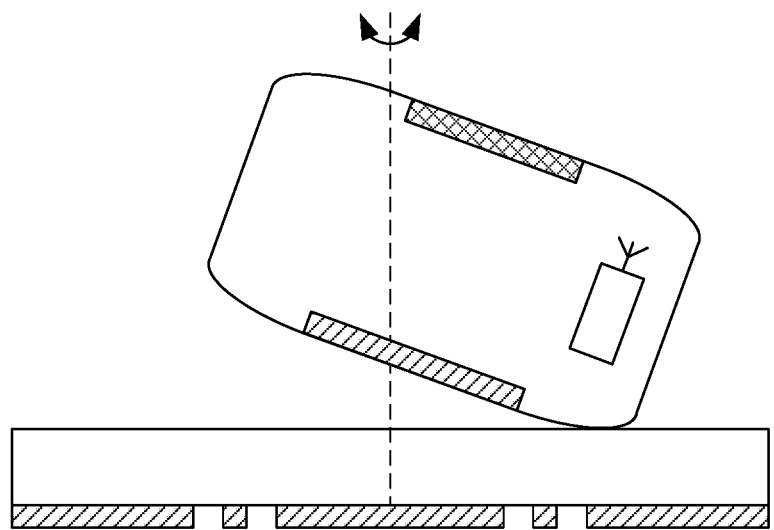

FIGS. 3a and 3b show in more detail the control device 36 according to some embodiments, when positioned on a control screen 30, 34.

The device 36 has a bottom surface 50, a top surface 52, and one or more side surfaces 54. In the illustrated embodiment, the device 36 is cylindrical (see FIG. 2 for example) although in practice it can take any shape. In some embodiments, the device 36 has chamfered edges 56 connecting at least the bottom surface 50 to the one or more side surfaces 54, so that the device 36 can be easily tilted.

The device 36 further comprises a wireless beacon 58 having an antenna 59. In some embodiments, the beacon 58 is a radio frequency ID tag. The beacon 58 may comprise a memory which can store identification data corresponding to the identity of the user of the device 36. The beacon 58 can further interact wirelessly with the detection systems 38, 40 in order to accurately locate the device 36 within the treatment room or the control room. Note that the systems 38, 40 can be located anywhere within the treatment room and control room respectively. For example, the system 38 may be arranged within the patient support 20.

The device 36 further comprises one or more magnetic elements 60 located in or near the bottom surface 50. The one or more magnetic elements 60 serve to secure the device 36 magnetically with respect to the control screen 30, 34, and also to allow the control screen to determine the device's orientation (e.g. its angle of rotation and its direction of tilt).

In the illustrated embodiment, the device further comprises a fingerprint reader 62 which may be located in or near the top surface 52. The device may also comprise a power source (not illustrated).

The screen 30, 34 comprises a display 64 which can be used to display a graphical user interface for controlling the system 10 as will be described below. None of the display circuitry is illustrated for clarity. A plurality of elements are arranged beneath the display 64, and these cooperate with the one or more magnetic elements 60 in the device 36 to determine the angle of rotation and tilt of the device 36, and to secure the device 36 to the screen 30, 34. For example, a magnetic element 66 is disposed beneath the device 36, with its polarity arranged so as to attract the one or more magnetic elements 60 in the device 36. In this way the device is secured to the screen 30, 34 (recalling that the screen 30, 34 may be placed at an angle as shown in FIGS. 1 and 2). Further, a plurality of magnetic sensors 68 are provided in order to detect the magnetic field generated by the one or more magnetic elements 60 and so determine the orientation of the device 36. This aspect is covered more fully in FIGS. 3b and 4. In an alternative or additional embodiment, resistive or capacitive touch or proximity sensors may be disposed in the vicinity of the device, which can be used to determine the tilt and/or position of the device.

Figure 4:
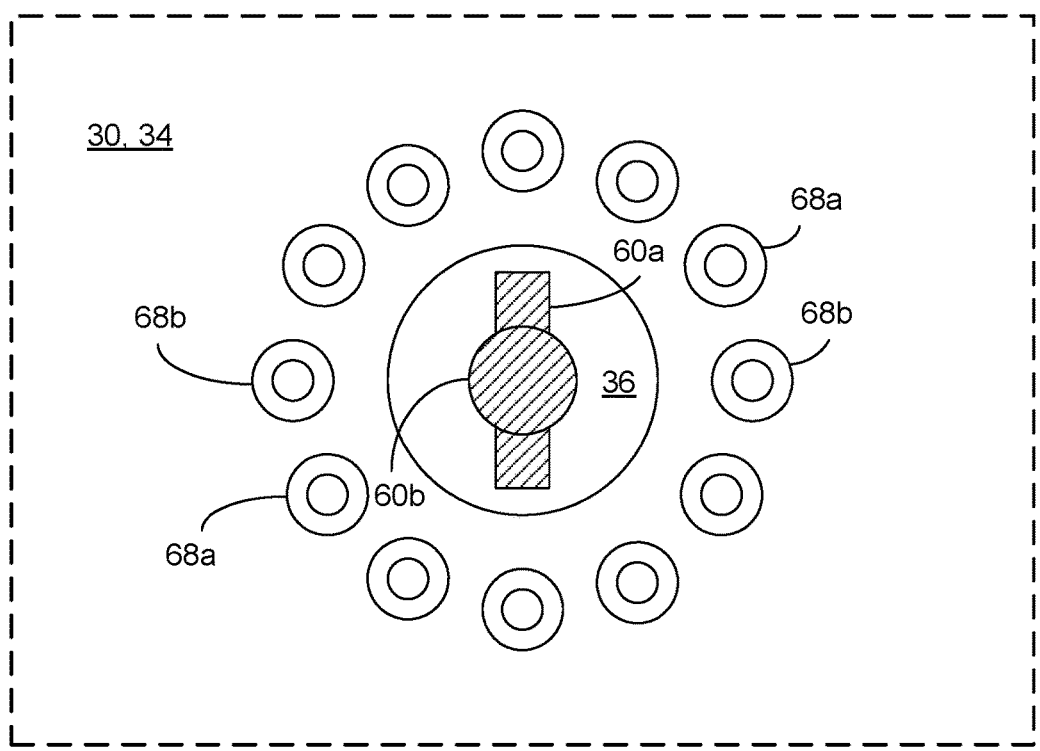
FIG. 4 is a plan view showing further detail of the control mechanism according to embodiments of the present invention.

FIG. 4 shows a bird's eye view of the control device 36 located on a portion of the control screen 30, 34. While the control screen includes a display 64, this is not illustrated for clarity in order to show the components of the screen 30, 34 beneath the display.

In the embodiment illustrated in FIG. 4, the one or more magnetic elements 60 within the device 36 comprise a first magnet 60a oriented substantially parallel to the bottom surface 50 (i.e. such that the magnetic moment lies substantially parallel to the bottom surface 50), and a second magnet 60b oriented substantially orthogonal to the bottom surface 50 (i.e. such that the magnetic moment lies substantially orthogonal to the bottom surface 50). The second magnet 60b is attracted by the magnetic field generated by the magnetic element 66 in the screen 30, 34, and this secures the device 36 to the screen 30, 34.

The screen 30, 34 comprises a plurality of magnetic sensors 68 arranged in a ring about the magnetic element 66. In some embodiments, the plurality of magnetic sensors are arranged in a plurality of pairs 68a, 68b of magnetic sensors, with sensors in each pair being arranged on opposite sides of the ring.

The magnetic field generated by the first magnet 60a is asymmetric in the plane of the sensors 68, and thus data from the sensors can be used to determine the angle of rotation of the device, i.e. the angle of rotation about the axis II. Further, as can be seen with respect to FIG. 3a, tilting the device 36 moves the ends of the first magnet 60a nearer and further from corresponding sensors of a sensor pair 68a. This tilt can therefore be detected by comparing the magnetic field sensed by corresponding sensors of the sensor pair 68a.

Figure 5:
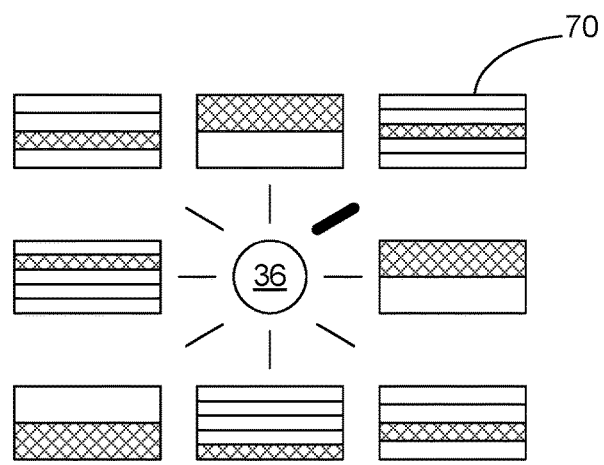
FIG. 5 shows part of a graphical user interface according to embodiments of the present invention.

The control device 36 can therefore be used to issue commands via the control screen by rotating the device 36 and/or by tilting the device 36. FIG. 5 illustrates an example graphical user interface employing these controls.

The device 36 is placed in a particular location on the screen 30, 34, above the magnetic element 66. One or more menus 70 are displayed on the screen around the device 36, with one of the menus being highlighted (in the top-right corner). In an embodiment, the user interface may only be displayed in response to the magnetic sensors 68 detecting the presence of a control device 36. When the device is removed, the user interface may also be removed. In the illustrated embodiment, each menu comprises a number of items and one item in each menu is highlighted. Each menu may correspond to a particular component of the system, and the items within the menu correspond to particular values or inputs for that component. Alternatively, each menu may correspond to a particular area of interest, such as the treatment plan, the system 10, the expected dosage profiles, etc, and clicking on each item within the menus may lead to further submenus opening. Those skilled in the art will appreciate that there are many different options for organizing the menu structure and the invention is not limited to any one of them.

By rotating the device around the axis II, the device 36 can be used to highlight a particular menu, or highlight a particular item within a menu, for example. By tilting the device 36 towards a particular menu or a particular item, that menu or item can be selected.

In use, the device 36 is associated with a particular radiotherapy professional. The association may be permanent (i.e. such that the device 36 belongs to a single professional and is not generally used by others) or transitory (i.e. such that the device 36 is associated with a single professional only for one or more sessions). The identity of the professional can be loaded into the device 36 through the beacon 58. For example, where the beacon 58 comprises an RFID tag, an RFID reader (not illustrated) can be used to load the data onto the device. In one embodiment, the identity of the professional can be confirmed through the fingerprint reader 62.

Each professional employed in the therapy suite will have a particular role which is associated with certain duties and responsibilities. For example, a qualified technician may need access to all regular controls of the system 10; a trainee technician may be allowed access only to a subset of those controls (e.g. not including the ability to commence treatment); a repair technician may require access to additional controls to allow effective maintenance of the system 10. Each user identity is therefore also granted a level of access to the system commensurate with that user's experience and role within the therapy suite.

In some embodiments, the menus displayed on the screen 30, 34 may therefore depend on the identity of the user associated with the particular device 36. The systems 38, 40 register the location of the device within the therapy suite, and also the identity of the user of the device 36. In some embodiments the systems 38, 40 may also identify whether that identity has been confirmed by the fingerprint reader 62. Once the information on the user identity is known, appropriate menus can be displayed on the screen 30, 34 around the device 36.

In other embodiments, the displayed menus may not depend on the identity of the user, but the user may be prevented from selecting or accessing controls where he or she is not authorised.

In some embodiments, the system 10 may record a log of which user makes which inputs using the device 36. Should an error occur, the log can be reviewed to determine which user input the incorrect commands.

In some embodiments, the menus displayed on the screen 30, 34 may also depend upon which screen the device 36 is placed. For example, in one embodiment, screens 30 on the patient support 20 may only display control information relating to the patient support 20. Thus when the device 36 is placed on one of those screens 30, the menus which are displayed allow the device to control the position and orientation of the bed 26 but not other aspects of the system 10. In contrast, the screens 34 in the control room may provide for control over more components of the system 10, or even the entire system 10.

Figure 6:
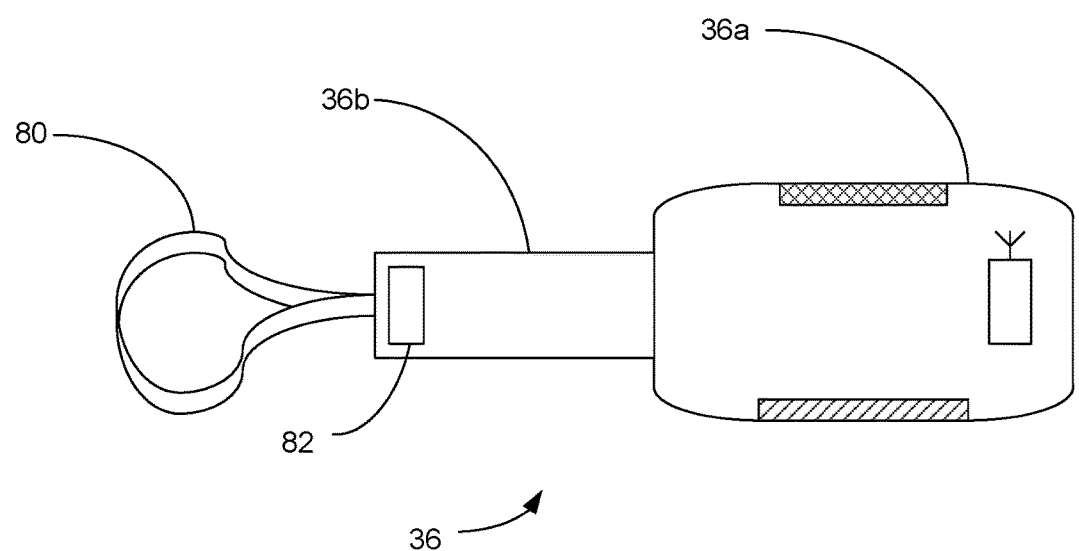
FIG. 6 shows a control device according to further embodiments of the invention.

As use of the device 36 can grant access to certain parts of the system 10, depending on the identity of the user, in some embodiments a mechanism is provided to ensure the device 36 remains attached to or within a certain distance of the user. For example, in one embodiment (see FIG. 6) the device 36 comprises two parts 36a, 36b. The first part 36a corresponds to the device as described in the embodiments of FIGS. 3a and 3b. The second part 36b comprises a cord 80 and a transceiver 82, and is detachably connected to the first part 36a. The cord 80 allows the device 36 to be worn around the user's neck or wrist so that the second part 36b at least remains attached to the user at all times. Those skilled in the art will appreciate that alternative means may be provided to attach the second part 36b to the user. In use, the first part 36a can be detached from the second part 36b, to allow the first part 36a to be placed on the control screens 30, 34 and used to control the system 10 in the manner described above. To ensure the first part 36a remains within the control of the user, the transceiver 82 may periodically transmit a polling signal to the first part 36a, and particularly the beacon 58. In response to the polling signal, the beacon 58 may transmit an answer signal which is received by the transceiver 82, thus ensuring that the first part 36a is not too distant from the second part 36b (and implicitly the user). If the answer signal is not received, or the signal is received with a signal strength which is below a threshold, the second part 36b may deem that the first part 36a is too distant from the user, and issue an alarm. For example, the second part 36b may vibrate, sound an alarm noise, or provide visual feedback.

Embodiments of the invention therefore provide a mechanism for controlling access to a radiotherapy system. In some embodiments, the mechanism allows control of the system only to those who are duly authorised and records which users make which inputs. Within the treatment room, the control mechanism is provided by way of one or more display screens which can be easily cleaned in contrast to conventional knobs and buttons.

Those skilled in the art will appreciate that various amendments and alterations can be made to the embodiments described above without departing from the scope of the invention as defined in the claims appended hereto.

We claim:

1. A patient support, comprising:
    a bed;
    one or more mechanisms configured for manipulating at least one of position and orientation of the bed;
    a display configured for displaying a user interface and receiving inputs to control at least the one or more mechanisms; and
    a mechanism configured for detecting an orientation of a control device on the display.

2. The patient support according to claim 1, wherein the display is provided on an edge of the bed.

3. The patient support according to claim 2, wherein the edge of the bed is located at the head of the bed or the foot of the bed.

4. The patient support according to claim 2, wherein the edge of the bed is sloped with respect to a plane of the bed.

5. The patient support according to claim 1, further comprising a mechanism configured for detecting the presence of a control device on the display.

6. A patient support comprising:
    a bed;
    one or more mechanisms configured for manipulating at least one of position and orientation of the bed;
    a display configured for displaying a user interface and receiving inputs to control at least the one or more mechanisms; and
    a detection system configured for determining an identity of a user of a control device on the display,
    wherein the display is configured to display input controls that are specific to the identity of the user determined by the detection system.

7. A radiotherapy system, comprising:
    a source of radiation configured to generate a beam of radiation;
    one or more collimating mechanisms configured to selectively delimit an extent of the beam of radiation;
    a patient support configured for supporting a patient undergoing radiotherapy, and including:
        a bed;
        a display configured for displaying a user interface and receiving inputs to control at least one of the source of radiation, the one or more collimating mechanisms, and the patient support; and
        a mechanism configured for detecting an orientation of a control device on the display.

8. The radiotherapy system according to claim 7, wherein the display is located on a console that is separate from the patient support.

9. The radiotherapy system according to claim 7, wherein the patient support comprises the display.

10. The radiotherapy system according to claim 7, further comprising a mechanism for detecting the presence of a control device on the display.

11. The radiotherapy system according to claim 7, wherein the one or more collimating mechanisms comprise a multi-leaf collimator.

12. A radiotherapy system comprising:
    a source of radiation configured to generate a beam of radiation;
    one or more collimating mechanisms configured to selectively delimit an extent of the beam of radiation;
    a patient support configured for supporting a patient undergoing radiotherapy, and including:
        a bed;
        a display configured for displaying a user interface and receiving inputs to control at least one of the source of radiation, the one or more collimating mechanisms, and the patient support; and
        a detection system configured for determining an identity of a user of a control device on the display,
        wherein the display is configured to display input controls that are specific to the identity of the user determined by the detection system.

* * * * *